United States Patent [19]
Siess

[11] Patent Number: 6,058,593
[45] Date of Patent: May 9, 2000

[54] METHOD FOR PRODUCING A MICRO MOTOR

[75] Inventor: Thorsten Siess, Wuerselen, Germany

[73] Assignee: Impella Cardiotechnick GmbH, Germany

[21] Appl. No.: 09/194,644

[22] PCT Filed: Mar. 31, 1998

[86] PCT No.: PCT/EP98/01867
   § 371 Date: Dec. 1, 1998
   § 102(e) Date: Dec. 1, 1998

[87] PCT Pub. No.: WO98/44619
   PCT Pub. Date: Oct. 8, 1998

[30]  Foreign Application Priority Data

Apr. 2, 1997  [EP]  European Pat. Off. ............. 08/832040

[51] Int. Cl.[7] .................................................. H02K 15/00
[52] U.S. Cl. ........................... 29/596; 29/598; 29/898.07; 310/43; 600/16
[58] Field of Search ............................. 29/596, 597, 598, 29/898, 447; 310/10, 42; 600/43, 16, 17, 18; 623/3

[56]  References Cited

U.S. PATENT DOCUMENTS 4,482,829  11/1984  Tardieu et al. .
   4,534,420   8/1985  Goldelius ................................... 173/12
   4,573,258   3/1986  Io et al. ..................................... 29/596
   4,862,582   9/1989  Henck ........................................ 29/596
   5,038,460   8/1991  Idle et al. .................................. 29/596
   5,121,021   6/1992  Ward ......................................... 310/154
   5,199,171   4/1993  Umezawa et al. ................... 29/898.07
   5,490,319   2/1996  Nakamura et al. ....................... 29/596
   5,584,114  12/1996  McManus ................................. 29/596
   5,894,653   4/1999  Nakamura et al. ....................... 29/596
   5,911,685   6/1999  Siess et al. ............................... 600/16
   5,921,913   7/1999  Siess ........................................ 600/16
   5,924,186   7/1999  Nakamura et al. .................... 29/602.1
   5,964,694  10/1999  Siess et al. ............................... 600/17

FOREIGN PATENT DOCUMENTS 0 361 775 A2   9/1989  European Pat. Off. .
   28 05 659 A1   2/1978  Germany .
   05328655       5/1992  Japan .

*Primary Examiner*—Jessica J. Harrison
*Assistant Examiner*—Minh Trinh
*Attorney, Agent, or Firm*—Fulwider Patton Lee & Utecht

[57]  ABSTRACT

A micro motor is manufactured by slipping the parts (24a, 24b) of a stator (24) on the mandrel (60) which is placed into an injection mold (50). The motor housing is made by injecting polymer material (63), the stator parts (24a, 24b) being encapsulated in the housing. During injection, a bearing (27) is contained in the injection mold (50). Subsequently, the mandrel (60) is drawn from the stator and a prepared rotor is inserted. Thus, a cost effective and high-precision manufacture of an electric motor with very small dimensions is made possible.

10 Claims, 1 Drawing Sheet

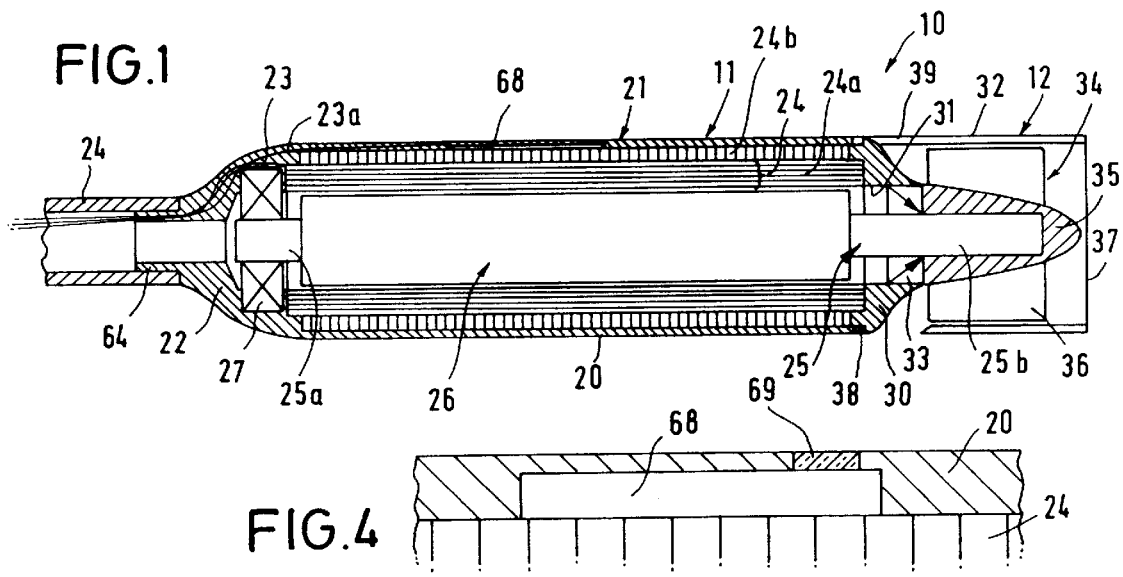
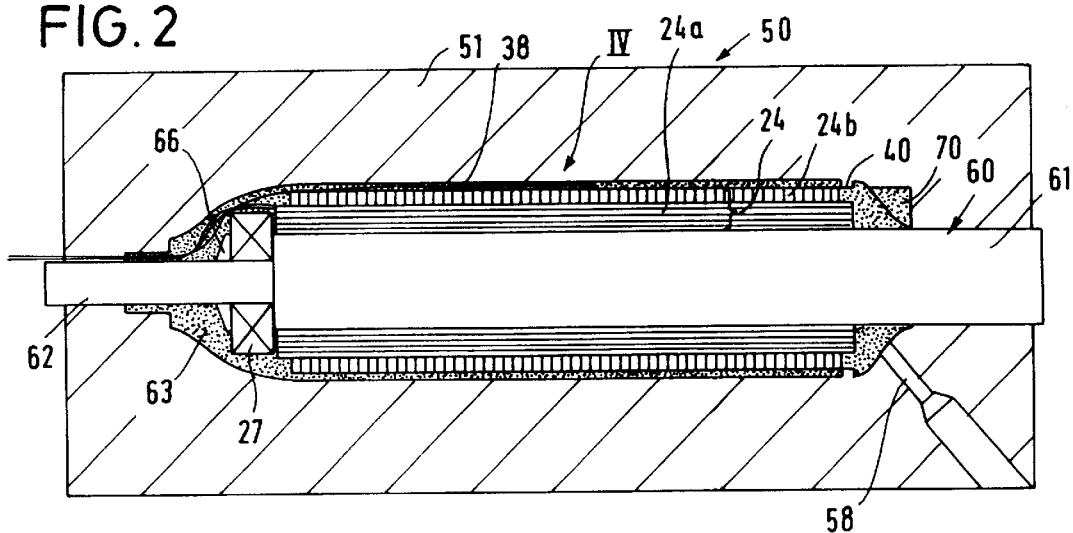
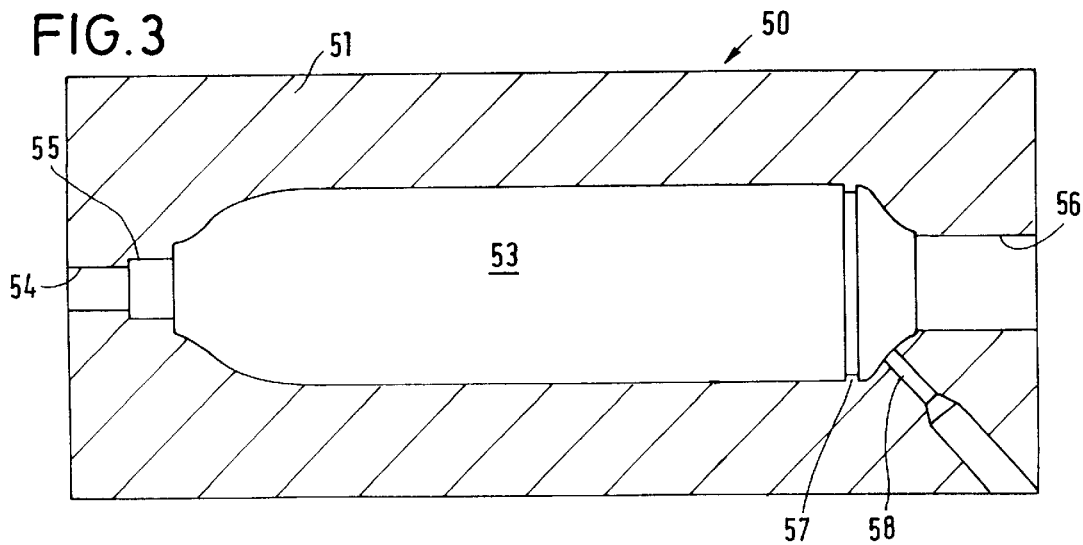

METHOD FOR PRODUCING A MICRO MOTOR

The present invention refers to a method for manufacturing a micro motor, in particular for a blood pump that may be operated in an intracardiac or intravascular manner.

Intravascular blood pumps are known that are introduced into the body by punctuating a blood vessel of the vascular system and subsequently advancing the blood pump through the blood vessel to the desired location inside the body. The maximum diameter of such elements introduced into blood vessels is limited since the pump has to be pushed through the blood vessel system from the introduction site to the application site. Further, the blood pump may only have small axial dimensions so that the pump is not obstructed when being advanced through bends of the vessel system. When a blood pump is advanced to the heart for assisting the left heart side, the outer diameter must not exceed 8.0 mm and the rigid length of the pump must not exceed 4 cm so that the pump can be pushed through the aortic arch into the heart.

From EP 0 157 871 D1 and EP 0 397 668, intravascular cardiac pumps are known, where the pump portion and the motor portion are constructed separately and are connected by a flexible shaft. While the pump portion is introduced into the body, the rotor portion remains outside the body.

WO94/09835 (Jarvik) describes a pump device for cardiac support, wherein at least one pump comprises a pump portion and a motor portion that are rigidly connected, the pump portion being introduced into one ventricle of the opened heart, whereas the motor portion remains outside the heart.

There is a need for intracardiac or intravascular pumps, i.e. pumps that may be arranged entirely and may be operated within the heart or a blood vessel, the motor portion and the pump portion thereof forming a rigid unit. However, this requires that each of both portions can be manufactured in extremely small size and with high precision.

In WO97/37696 (published posteriorly), an intravascular blood pump is described, wherein the drive portion and the pump portion form a rigid unit connected to a catheter. The dimensions of the blood pump are small enough to allow for the pump to be pushed through a blood vessel to the destination or to be operated in the blood vessel. In the intravascular blood pump, the pump portion and the drive portion are of substantially the same diameter of no more than about 5–7 mm. In addition, the pump may be prolongated by means of a flexible hose extending its effective length.

In a blood pump to be operated within the body, high precision is required from the drive and pump portions. In particular, it must be guaranteed that the impeller of the rotary pump is very accurately centered in the pump housing and that the pump housing is also very accurately positioned with respect to the motor housing. When these requirements are not met exactly, damage to the blood and thrombogenesis may occur due to shear forces. On the other hand, it must be taken into consideration that such blood pumps are generally used as one-way articles and, therefore, should be economical to manufacture.

It is the object of the present invention to provide a method for manufacturing a micro motor for use in a blood pump, the method allowing to manufacture a micro motor at low cost and with high precision.

According to the invention, the object is solved with the features of claim 1.

In the present method, the stator of the motor is manufactured by pushing the stator parts onto a mandrel and placing them into an injection mold together with the mandrel. Polymeric material is injected into the injection mold, the material enclosing the stator parts and later forming the motor housing. Thus, a stator centered on the mandrel is obtained, which has its parts embedded in a housing that is also centered on the mandrel. The mandrel may be positioned very accurately in the injection mold. In general, the stator parts are coils and soft-iron yoke sheets for magnetic yokes. The present method makes it possible to strictly meet rigorous tolerance requirements by not building the stator from the outside inward, as it is usually done, but from the inside outward. The centering is effected with the mandrel on which the stator parts are mounted first, the housing being formed subsequently. After the mandrel has been removed, the mandrel may be replaced with a motor rotor which would then be positioned very precisely.

Suitably, the polymer material used has such a low viscosity that it encloses the individual parts and even penetrates into the narrowest gaps so that the individual parts are not only encapsulated but firmly interconnected. Thus, the individual windings and stator sheets are glued to form an integral unit. Particularly suited for use in the manufacture of an intravascular blood pump is a biocompatible two component epoxy resin.

In a preferred embodiment of the method, a bearing is set onto a mandrel, which is placed into the injection mold together with the mandrel. To prevent the bearing from becoming filled with the polymeric mass, it may be filled with a removable material such as wax or silicone grease that eventually bleeds out or serves as a lubricant for the bearing.

The present method is particularly suited for an electronically commutated synchronous motor, wherein the rotor includes at least one permanent magnet, whereas the stator comprises coil windings. The rotor comprised of a shaft, the magnet and a seal forms a unit that may be introduced as a whole into the motor housing, the insertion opening eventually being closed by the seal forming part of the unit. The impeller of the pump may also be an integrating part of the rotor unit.

Preferably, the motor housing is manufactured with an opening corresponding to the cross-section of the rotor to be inserted, the rotor being pushed through this opening and having its shaft provided with a bearing that closes the opening. This makes it possible to form the micro motor of only two elements. Therefore, the micro motor can be manufactured in a simple manner and at low cost, and it is further suited for use as a one-way article.

The following is a detailed description of an embodiment of the invention with reference to the accompanying drawings.

In the Figures:

FIG. 1 is a longitudinal section through the micro motor to be manufactured and the pump, FIG. 2 a longitudinal section through the injection mold during the manufacture of the motor housing, FIG. 3 shows a longitudinal section through the empty injection mold, and FIG. 4 is an enlarged illustration of the detail IV in FIG. 2.

FIG. 1 illustrates an intravascular blood pump 10, i.e. a blood pump that may be pushed through the blood vessel system of a patient to eventually enter the heart. The outer diameter of such a blood pump is nowhere larger than 7 mm.

The pump 10 comprises a drive portion 11 and a rigidly connected pump portion 12. The drive portion 11 has an electric micro motor 21 having an elongate cylindrical housing 20. At the rear end, the housing 20 is closed with an end wall 22 which is followed by a flexible catheter 14 sealing the same. The electric lines 23 for power supply and for controlling the electric motor 21 and further lines 23a connected to the sensors of the pump 10 extend through this catheter 14.

As is typical, the stator 24 of the motor has a plurality of circumferentially distributed coils 24a and a magnetic yoke 24b made of sheet metal and arranged in the longitudinal direction. It is enclosed by the motor housing 20 injection molded therearound. The stator 24 surrounds the rotor 26 connected with the motor shaft 25 and made of permanent magnets magnetized in the active direction. A bearing 27 supports the rear end of the motor shaft in the motor housing or the end wall 22. The motor shaft extends throughout the entire length of the motor housing 20 and projects therefrom to the front.

The front closure of the motor housing is formed by a tubular stationary hub member 30 which is an integrated part of the housing 20. The outer diameter of the hub member tapers towards the front end where a bearing 33 for supporting the motor shaft 25 is situated. This bearing is simultaneously designed as a shaft seal.

The motor shaft 25 protrudes forward from the hub member 30, where it carries an impeller wheel 34 with a hub 35 sitting on the shaft end and blades 36 or pump vanes protruding obliquely therefrom with respect to the axis of the impeller wheel 34. The impeller wheel 34 is accommodated in a cylindrical pump housing 32 connected by three circumferentially distributed struts 39 to a ring 38 sitting on the hub member 30. It is obvious that the motor housing 20 and the pump housing 32 are rigidly interconnected and have equal outer diameters, and that the diameter of the pump 10 is nowhere larger than this outer diameter.

When the impeller wheel 34 rotates, blood is drawn through the intake opening 37 of the pump housing 32 and forced rearward in the axial direction in the pump housing 32. Through the annular gap between the pump housing 32 and the motor housing 20, blood flows outward along the hub member 30 to further flow along the motor housing 20. Thereby, the heat generated in the drive is carried away without the blood being damaged by excessively high surface temperatures (above 41° C.) on the motor housing 20.

It is also possible to design the pump portion 12 for the opposite delivery direction, the blood being drawn along the motor housing and being discharged axially at the front end opening 27.

A pressure sensor 68 is embedded in the peripheral wall of the motor housing 20, the sensor being connected with a line 23a. This line 23a is encapsulated in the motor housing 20 and extends through the end wall 22 into the catheter 24. At the proximal end of the catheter, the lines 23a and the cable 23 may be connected to an extracorporeal control device that controls the operation of the pump 10.

The manufacture of the micro motor 21 is effected in a simple injection molding process using the injection mold illustrated in FIG. 3. This injection mold 50 comprises two mold halves 51 that may be moved apart and, when assembled, enclose a mold cavity 53, the contour of which corresponds to the outer contour of the housing 20.

An axial bore 54 extends from the mold cavity 53, the bore being connected with the mold cavity 53 via a step portion 55 of enlarged diameter.

At the opposite end, an axial bore 56 is provided which has a diameter approximately as large that of the rotor 26. Further, the mold cavity 53 is formed with a circumferentially extending projection 57 so as to form an annular groove 40 in the motor housing. Injection channels 58 extend into the mold cavity 53 for injecting resin into the mold.

When manufacturing the micro motor, the mandrel 60 illustrated in FIG. 2 is used. The same is a cylindrical rod 61 with a length greater than that of the stator 24. Adjoining the one end of the rod 61 is a cylindrical projection 62 of reduced diameter which fits exactly into the bore 54 of the injection mold 50. The cylindrical rod 61 fits exactly into the axial bore 56 so that an exact centered position of the mandrel 60 can be safely achieved.

The bearing 27 is fitted onto the projection 62. The parts 24a, 24b of the stator 24 are set onto the rod 61. Then, the mandrel 60 with the parts 24a, 24b of the stator 24 and the bearing 27 is placed into the mold half 51 and the injection mold is then closed by installing the second mold half. Subsequently, resin is injected into the mold cavity 53, with those cavities not filled by parts on the mandrel 60 being filled with polymer material 63 to form the housing 20 with the end wall 22 and the hub member 30. In the area of the step 55, a sleeve 64 is formed (FIG. 1) onto which the catheter 24 may be slipped. The wires 23 and the line 23a extend through this sleeve 64. The hub member 30 is also formed from the injected polymer material, as well as the circumferential wall of the housing 20. An opening 31 is made in the hub member 30 (FIG. 1) that is as large as the channel enclosed by the stator 24. Moreover, an annular groove 40 is formed at the circumference of the hub member 30 (FIG. 2), into which the ring 38 of the pump housing 32 is snapped.

For preventing the bearing 27, which is a roller bearing, from being filled during injection of the polymer material, the bearing is filled with a removable material such as wax or silicone grease which later flows out or serves as a bearing lubricant. Moreover, a free space 66 (FIG. 2) is kept free with a corresponding filling material to guarantee the free running of the bearing 27.

Among the parts of the stator 24, encapsulated with the polymer material 63 is the sensor 68 (FIG. 4) which in this case is a pressure sensor. A plug 69 keeps the pressure window of the sensor 68 free. This plug 69 is eventually removed.

The injection mold further comprises cavities for radial ribs 70 (FIG. 2) provided at the bevel of the hub member 30. These ribs serve to support the struts 39 of the pump housings 32 and they are inclined in the direction of the flow. The ribs 70 cause the pump housing 32 to exactly maintain its axial orientation despite the thin wall thickness of the struts 39.

After the polymer material 63 has cured, the mold halves are disassembled and the motor housing 20 is drawn from the mandrel 60 with the stator 24 contained therein. Then, the rotor 26 is introduced through the opening 31, the end 25a of the shaft 25 entering the bearing 27. At the opposite end 25b of the shaft 25, the bearing 33 is provided which at the same time acts as a seal. Upon inserting the rotor, the bearing 33 sitting on the shaft is fitted into the opening 31 of the motor housing 20. Thereby, the distal end of the motor housing is sealed off. On the end of the shaft 25 protruding from the seal 33, the impeller wheel 34 mounted before is provided. Eventually, the pump housing 32 with the ring 38 fastened to the struts 39 is snapped into the annular groove 40 of the motor housing 20.

The diameter of the mandrel 60 is about $2/10$ mm larger than that of the rotor 26 so that an air gap of only $1/10$ mm is formed between the rotor and the stator. Such a small air gap is readily achieved with the above described manufacturing and assembling method.

What is claimed is:

1. A method for manufacturing a micro motor (21), the method comprising the following steps:

slipping stator parts (24a, 24b) onto a rigid mandrel (60), placing the mandrel (60) with the stator parts (24a, 24b) into an injection mold (50), injecting a polymer material (63) into the injection mold (60) for forming a motor housing (20), removing the injection mold (50) and the mandrel (60) from the motor housing (20), inserting a rotor (26) into the motor housing (20), the outer diameter of the rotor (26) being slightly smaller than that of the mandrel (60).

2. The method of claim 1, further comprising the step of slipping a bearing (27) onto the mandrel (60) before placing the mandrel (60) into the injection mold (50).

3. The method of claim 2, further comprising the step of filling the bearing (27) with a removable material to avoid the filling of the bearing (27) with polymer material.

4. The method of claim 3, wherein the removable material comprises wax or a similar substance easy to melt or to remove with a solvent.

5. The method of claim 1, wherein the mandrel which has two ends (60) is inserted into the injection mold (50) from one end, while the other end is supported in a channel (54) of the injection mold (50) and an end wall (22) is formed to the motor housing (20) at the other end.

6. The method of claim 1, wherein the outside of the stator parts (24a, 24b) is provided with at least one sensor encapsulated within said polymer material (63).

7. The method of claim 6, wherein the sensor (68) is partly covered with a cover (69) which is removed after encapsulation.

8. The method of claim 1, wherein the motor housing (20) is manufactured with an opening (31) corresponding to the diameter of the rotor (26) to be installed, through which opening the rotor (26) is inserted, the shaft (25) of the rotor being provided with a bearing (33) closing the opening (31).

9. The method of claim 1, wherein radial ribs (70) are formed by injection molding on one end of the motor housing (20), the ribs being used as supports for the struts (39) of a pump housing (32).

10. The method of claim 1, characterized in that power lines (23) and/or information lines (23a) are encapsulated with the polymer material (63).

* * * * *